(12) United States Patent
Karicherla

(10) Patent No.: US 7,289,856 B1
(45) Date of Patent: Oct. 30, 2007

(54) MEDICAL ELECTRICAL LEAD CONTAINING A PYROELECTRIC MATERIAL

(75) Inventor: Annapurna Karicherla, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 266 days.

(21) Appl. No.: 10/954,333

(22) Filed: Sep. 29, 2004

(51) Int. Cl.
*A61N 1/00* (2006.01)

(52) U.S. Cl. .................. 607/122; 607/120; 607/116

(58) Field of Classification Search ............ 607/119, 607/121, 122, 120
See application file for complete search history.

(56) References Cited

U.S. PATENT DOCUMENTS

| | | | |
|---|---|---|---|
| 4,953,564 A * | 9/1990 | Berthelsen | 607/120 |
| 5,730,134 A * | 3/1998 | Dumoulin et al. | 600/412 |
| 5,871,449 A | 2/1999 | Brown | 600/474 |
| 6,640,137 B2 | 10/2003 | MacDonald | 607/35 |
| 7,065,411 B2 * | 6/2006 | Verness | 607/116 |
| 2002/0138113 A1 | 9/2002 | Connelly et al. | 607/36 |
| 2004/0015069 A1 | 1/2004 | Brown | 600/407 |

OTHER PUBLICATIONS

Furukawa, T. Piezoelectricity and Pyroelectricity in Polymers, IEEE Transactions on Electrical Insulators, vol. 24 issue 3, Jun. 1989, pp. 375-394.*

* cited by examiner

*Primary Examiner*—Carl Layno
*Assistant Examiner*—Brian T. Gedeon

(57) ABSTRACT

A medical electrical lead containing a pyroelectric material is provided. The pyroelectric material is capable of dissipating heat generated in the lead due to radio frequency energy. The pyroelectric material may be a polymeric material, such as polyvinylidene fluoride (PVDF).

21 Claims, 3 Drawing Sheets

MEDICAL ELECTRICAL LEAD CONTAINING A PYROELECTRIC MATERIAL

FIELD OF THE INVENTION

The present invention relates generally to implantable medical devices for providing stimulating pulses to selected body tissue, for example, the heart, and more particularly, to the lead assemblies connecting such devices with the tissue to be stimulated.

BACKGROUND OF THE INVENTION

Although it will become evident to those skilled in the art that the leads described are applicable to a variety of implantable medical devices utilizing pulse generators to stimulate selected body tissue, the leads and their background will be described principally in the context of a specific example of such devices, namely, cardiac pacemakers or defibrillators for providing precisely controlled stimulation pulses to the heart. However, the appended claims are not intended to be limited to any specific example or embodiment described herein.

Pacemaker leads form the electrical connection between the cardiac stimulator and the heart tissue which is to be stimulated. As is well known, the leads connecting such cardiac stimulators with the heart may be used for pacing, for sensing electrical signals produced by the heart, for defibrillation, or for a combination of those procedures in which case a single lead serves as a bidirectional pulse transmission link between the stimulator and the heart. An endocardial type lead, that is, a lead which is inserted into a vein and guided therethrough into a cavity of the heart, includes at its distal end an electrode designed to contact the myocardium. The lead further includes a proximal end having a connector pin adapted to be received by a mating socket in the pacemaker. A flexible, maybe coiled, conductor or plurality of conductors surrounded by an insulating tube or sheath typically couples the connector pin at the proximal end and the electrodes at or near the distal end. An epicardial lead is similar to the endocardial lead in terms of construction; however, the lead is connected to the myocardium via the outer surface of the heart.

Implantable cardiac stimulation leads may take the form, for example, of pacemakers capable of pacing and sensing in at least one chamber of the heart. Indeed, embodiments may relate to a programmable dual chamber pacemaker wherein the basic configuration of the pacemaker, e.g. unipolar or bipolar, can be changed, including the grounding configuration and ground potentials used within the pacemaker.

Generally, a heart stimulator uses one or two flexible leads having one end connected to the device and the other end connected to electrodes placed in close proximity to the heart. These leads are used to stimulate or pace the heart. Also, these leads are used to sense the heart activity by picking up electrical signals from the heart.

In order to properly pace or sense or defibrillate, the cardiac stimulator device has to be able to deliver a stimulating pulse to the heart or to sense an electrical signal from the heart. This requires that there be an electrical return path. If, within a given heart chamber, a unipolar lead is used containing a single conductor, the return path comprises the conductive body tissue and fluids. The return path is connected to the stimulator device by connecting the stimulator device's electrical common or ground to the stimulator's metal enclosure, typically referred to as the case or housing. The case or housing, in turn, makes contact with the body tissue and/or fluids. Pacing or sensing using the pacer case or enclosure as part of the electrical return path is known as unipolar pacing or sensing.

An alternative solution to using a unipolar lead in a given heart chamber is to use a double lead/electrode in the heart chamber, known as a bipolar lead. In a bipolar lead, a second conductor is spiraled over and insulated from a first conductor along the length of the lead. At the distal end of the lead, one of the conductors is connected to a first electrode, referred to as the "tip" electrode, and the second conductor is connected to a second electrode, referred to as a "ring" electrode. The ring electrode is generally situated about 10 to 20 mm proximally from the tip electrode. The tip electrode is typically placed in contact with heart tissue, while the ring electrode is in electrical contact with the blood, and in some instances can also be in contact with heart tissue. Because body and heart tissue and fluids are conductive, the ring electrode of a bipolar lead, in contact with the body fluids or tissue, serves as an electrical return for both pacing and sensing. Pacing or sensing using the lead ring electrode and associated lead conductor as the electrical return path is known as bipolar pacing or sensing.

There are numerous factors to consider when deciding whether unipolar or bipolar pacing and/or sensing should be used. Bipolar pacing has, in general, the advantage of requiring slightly less energy than unipolar pacing, and with regard to sensing, bipolar pacing impedance is usually greater than unipolar impedance. Further, bipolar sensing is less prone to far-field signals, crosstalk, and myopotential sensing than is unipolar sensing since its dipole is so much smaller. Crosstalk generally refers to a pacer mistakenly sensing a heart activity in one heart chamber immediately after the other chamber is paced. Bipolar sensing reduces crosstalk resulting from a pacing stimulus in the opposite chamber. Bipolar pacing is preferred if pectoral or diaphragmatic stimulation occurs.

Radio frequency energy can be a potentially dangerous phenomenon for a patient having an implantable medical device. For example, during Magnetic Resonance Imaging (MRI), localized heating effects have been observed near metallic implants in the body. The intra cardiac lead body in an implantable cardiac device system has metallic conducting wires that transmit electrical pulses to the desired location in the heart. During MRI, localized heating has been observed due to the presence of these leads in the body, particularly at the tip of the intra cardiac lead. In many cases, heating is extreme and potentially dangerous.

Radio frequency energy that is inductively coupled into the lead may cause intense heating along the length of the wire and at the electrodes that are attached to the heart wall. This heating may be sufficient to ablate the interior surface of the blood vessel through which the wire lead is placed, and may be sufficient to cause scarring at the point where the electrodes contact the heart, or elevate the patient's body temperature and cause fever.

Thus, there is a need to provide an implantable medical device for which possible damage to the patient or fever due to localized radio frequency heating is minimized or prevented.

SUMMARY

A medical electrical lead that protects against localized heating generated from radio frequency energy is disclosed. A medical electrical lead comprises a first electrical conductor extending from the proximal end to the distal end of the lead. An electrical connector is coupled to the first conductor at the proximal end of the lead. A first electrode is coupled to the lead at the distal end of the lead. A biocompatible pyroelectric material is coupled to the lead near the distal end of the lead. The medical electrical lead may further comprise a second electrical conductor that is coupled to the electrical connector and extends to and is coupled to a second electrode disposed near the distal end of the lead, proximate the first electrode. The pyroelectric material includes a polymeric material, such as polyvinylidene fluoride (PVDF).

A method of making a medical electrical lead capable of protecting against localized heating generated from radio frequency energy, by dissipation of the heat is also disclosed. The method comprises providing a medical electrical lead including a first electrical conductor, an electrical connector coupled to the first conductor at the proximal end of the lead, and a first electrode coupled to the conductor at the distal end of the lead, and applying a biocompatible pyroelectric material to the lead near the distal end. The medical electrical lead may be further provided with a second electrical conductor which is coupled to the electrical connector and extends to and is coupled to a second electrode which is near the distal end of the lead, proximate of the first electrode.

Further features, advantages, and benefits will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate typical embodiments, and together with the description, serve to explain the principles of the invention in general terms.

BRIEF DESCRIPTION OF THE FIGURES

The foregoing aspects and other features are explained in the following description, taken in connection with the accompanying figures, wherein.

DETAILED DESCRIPTION

Figure 1:
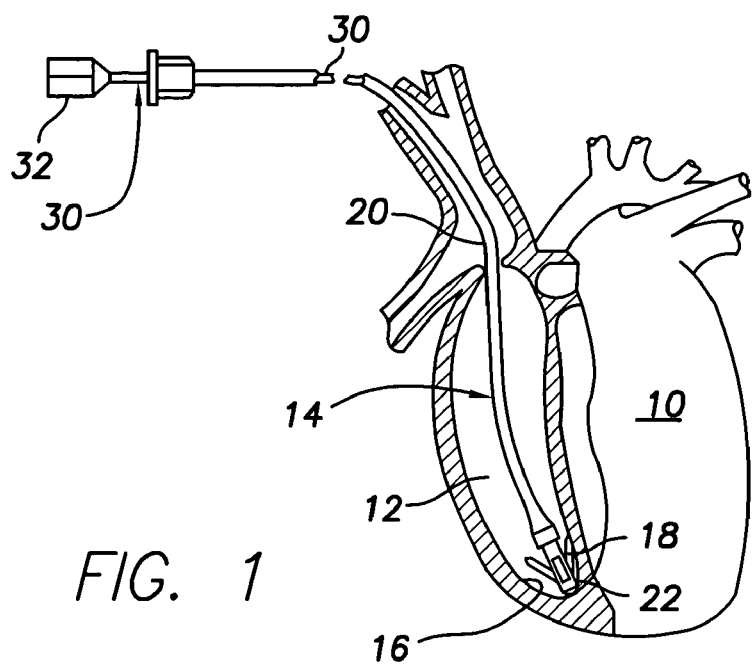
FIG. 1 is a perspective view illustrating a heart with a portion cut away to reveal an implantable lead assembly, secured therein to a wall of the heart.

The following detailed description refers to the accompanying drawings that illustrate exemplary embodiments. Other embodiments are possible, and modifications may be made to the embodiments within the spirit and scope of the present invention. Therefore, the following detailed description is not meant to be limiting. Rather, the scope of the invention is defined solely by the appended claims.

In one embodiment, a medical electrical lead includes an electrical conductor extending from the proximal end to the distal end of the lead, an electrical connector coupled to the conductor at the proximal end of the lead, an electrode coupled to the conductor at the distal end of the lead, and a biocompatible pyroelectric material coupled to the lead near the distal end of the lead.

For example, a medical electrical lead includes a first electrical conductor extending from the proximal end to the distal end of the lead, an electrical connector coupled to the first conductor at the proximal end of the lead, a first electrode coupled to the conductor at the distal end of the lead, and a biocompatible pyroelectric material coupled to the lead near the distal end of the lead. Illustratively, the medical electrical lead is a unipolar lead having a biocompatible pyroelectric material coupled to the lead near its distal end.

Alternatively, the medical electrical lead further includes a second electrical conductor which is coupled to the electrical connector and extends to and is coupled to a second electrode which is near the distal end of the lead, proximate the first electrode. Illustratively, the medical electrical lead is a bipolar lead having a biocompatible pyroelectric material coupled to the lead near its distal end.

In another embodiment, a medical electrical lead capable of dissipating heat generated from radio frequency (RF) energy can be made by providing a medical electrical lead having an electrical conductor, an electrical connector coupled to the conductor at the proximal end of the lead, and an electrode coupled to the conductor at the distal end of the lead, and applying a biocompatible pyroelectric material which dissipates heat generated when subjected to RF energy to the lead near the distal end. The pyroelectric material dissipates heat by absorbing and converting the heat to voltage.

For example, a medical electrical lead can be made by providing a medical electrical lead having a first electrical conductor, an electrical connector coupled to the first conductor at the proximal end of the lead, and a first electrode coupled to the conductor at the distal end of the lead, and applying a biocompatible pyroelectric material, which dissipates heat generated when subjected to RF energy, to the lead near the distal end. Illustratively, the medical electrical lead is made applying a biocompatible pyroelectric material to a unipolar lead near its distal end.

Alternatively, the medical electrical lead may be further provided with a second electrical conductor, which is coupled to the electrical connector and extends to and is coupled to a second electrode which is near the distal end of the lead, proximate the first electrode. Illustratively, the medical electrical lead is made by applying a biocompatible pyroelectric material to a bipolar lead near its distal end.

Referring now to the drawings, FIG. 1 illustrates a diagrammatic perspective view, partially cut away and shown in section, of a heart 10 into the right ventricle 12 of which is inserted an implantable medical electrical lead 14 of the endocardial type containing a pyroelectric material (not shown). The lead 14 is attached to an interior wall 16 of the heart 10 by means of fixing tines 18, for example, which engage the tissue or trabeculae of the heart.

Figure 2:
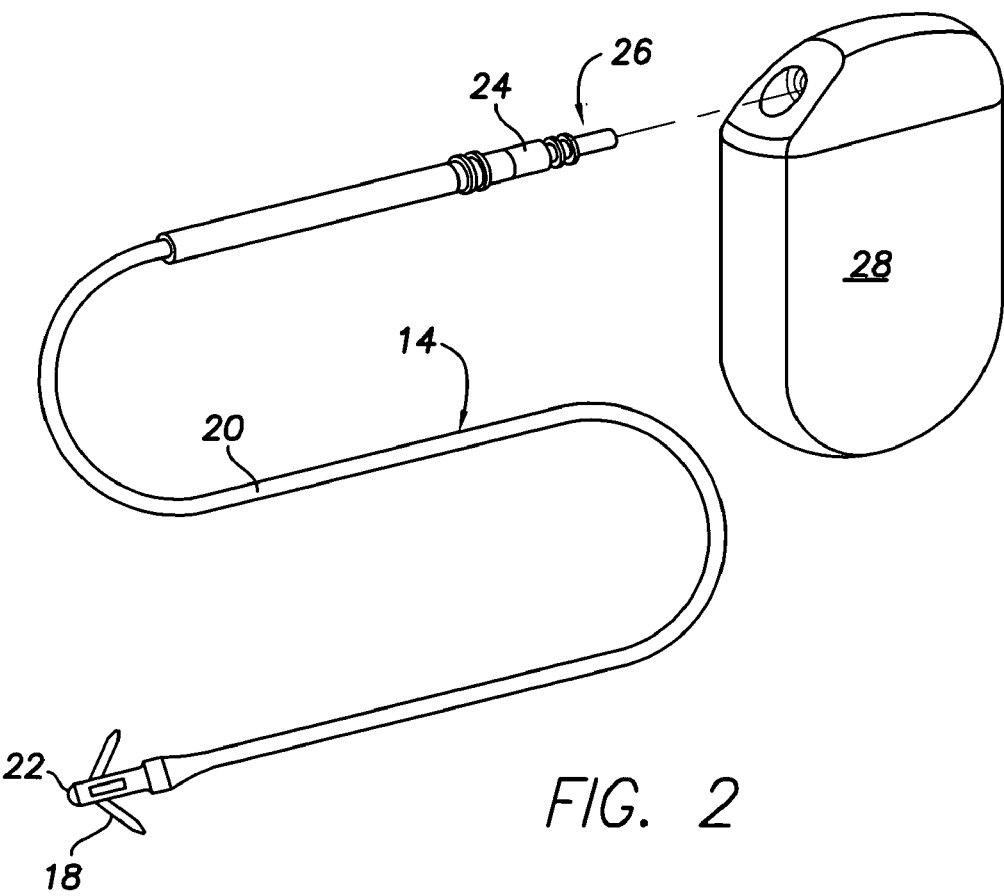
FIG. 2 is a perspective view of an implantable lead in combination with a stimulating device such as a pacemaker.

Lead 14 also includes an insulative sheath 20 interconnecting a distal electrode 22 secured adjacent the interior wall 16 and an electrical connector 24 (see FIG. 2) at a proximal end 26 to which can be attached a source of electrical energy such as a pacemaker 28. In FIG. 1, a stylet 30 is illustrated inserted within the insulating sheath 20 with the aid of a manipulating device 32 and may be used to provide rigidity to the lead 14 during insertion of the lead into the heart 10.

Referring to FIG. 3, lead body 34 of an illustrative bipolar lead has a proximal end (not shown) and a distal end 36. At the distal end is tip electrode 38. A pyroelectric material 40 is coupled to the lead body between the tip electrode 38 and the ring electrode 42.

The conductors of the leads typically comprise metals, such as, e.g., MP35N alloy, stainless steels, Elgiloy® alloy, and/or DBS/MP. However, in some embodiments, one or more of the conductors may be a non-metal.

Lead electrodes (e.g. ring and tip electrodes for a bipolar lead, or a distal electrode for a unipolar lead) are typically metals. A suitable metal for the electrodes includes titanium nitride-coated platinum-iridium. However, suitable non-metallic materials may be employed.

Lead body 34 typically includes an insulative sheath (not shown). The insulative sheath may be any suitable insulating material. For example, the insulative sheath may be silicone rubber or polyurethane-based material such as, for example, Pellethane®80A and Pellethane® 55D polyurethanes (Dow Chemical Company), Pursil™ (Polymer Technology Group, Berkeley, Calif.) and Elast-Eon 2A™ (Aortech Biomaterials, Melbourne, Australia).

The pyroelectric material that may be used in the medical electrical lead is not particularly limited, so long as it is biocompatible (including a material that is rendered biocompatible) and exhibits properties of a pyroelectric material. Pyroelectric materials become electrically polarized upon an applied temperature change. Thus, the pyroelectric material is capable of dissipating heat generated by radio frequency energy by absorbing the heat and converting such heat into an electrical charge. Illustrative suitable pyroelectric materials include ceramics and polymeric materials.

In embodiments of the lead, the pyroelectric material is a polymeric material, such as, for example, polyvinylidene fluoride (PVDF). PVDF is a pyroelectric polymer which responds to a thermal gradient with redistribution in electronic charge in the material, thereby generating voltage. As a polymer, PVDF can easily be made into different shapes and sizes, including films.

Illustratively, polyvinylidene fluoride can be analogized as an electrical sponge in terms of its piezoelectric effect and as a thermal sponge for its pyroelectric behavior. Once the PVDF material absorbs its maximum heat capacity, the pyroelectric material converts the heat into voltage. Once the conversion from heat to voltage has been completed, the PVDF material can absorb more heat.

The pyroelectric material may be typically coupled to the lead near the distal end of the lead. By "coupling" of the pyroelectric material "near the distal end of the lead," it is meant that the pyroelectric material is in contact with the interior and/or exterior of the lead body, at or in proximity to the distal end of the lead, so as to be able to absorb and dissipate heat generated or transferred to the distal end of the lead due to radio frequency energy.

Much, if not most of the radio frequency energy is transferred to exposed metallic parts of the lead, most particularly the tip of the lead at its distal end. Thus, the pyroelectric material is coupled to the lead near the tip (distal) electrode in order to dissipate the heat generated by radio frequency energy due to, for example, an MRI. The phrase "near the tip (distal) electrode" is intended to encompass embodiments where the pyroelectric material is in contact with the tip/distal electrode.

In embodiments where the pyroelectric material is incorporated into a bipolar lead, the pyroelectric material can be in contact with the interior and/or exterior of the lead body in a location between the ring electrode and the tip electrode.

The phrase "between the ring electrode and the tip electrode" is intended to encompass embodiments in which the pyroelectric material is in contact with the ring electrode, the tip electrode, or both.

Figure 3A:
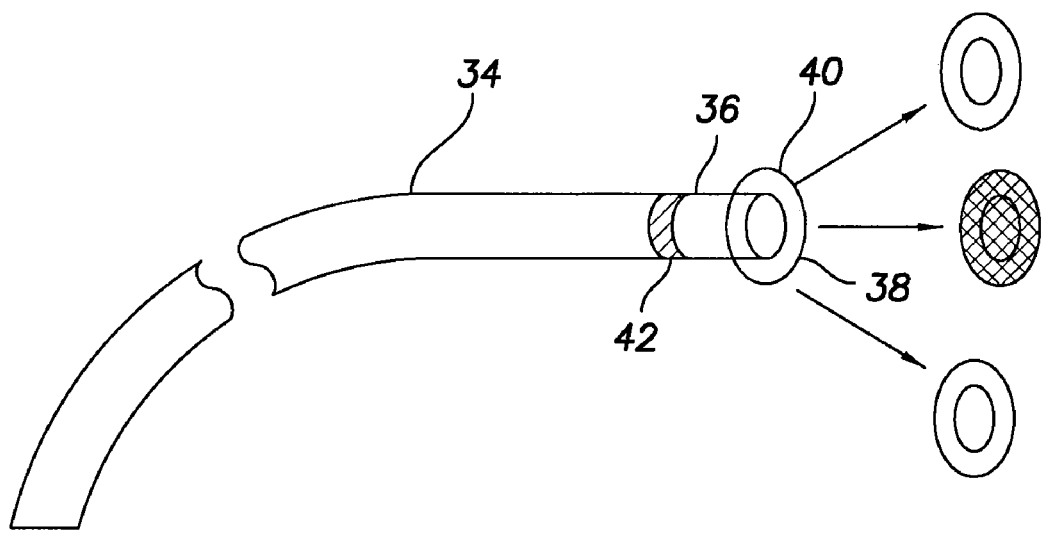
FIG. 3A is a simplified, perspective view of an illustrative lead body containing a pyroelectric material.
Figure 3B:
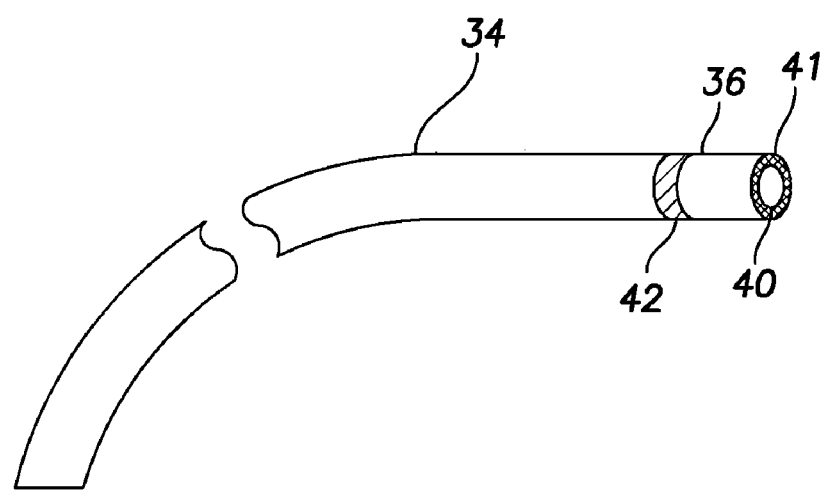
FIG. 3B is a simplified, perspective view of another illustrative lead body containing a pyroelectric material.

As illustrated in FIG. 3A, the pyroelectric material can be incorporated into the lead in a variety of ways. For example, the pyroelectric material 40 can be coupled to the lead as a film, mesh, or disk attached to the lead body 34. Illustratively, the pyroelectric material 40 can be fixed in the form of a mesh, similar to the type used in epicardial leads, near the distal end of the lead, as illustrated in FIG. 3A. In FIG. 3B, the pyroelectric material 40 can also be coupled to the lead as a collar 41 attached to the lead body 34. The pyroelectric material may be mounted on the insulative sheath of the lead at its distal end, such as, for example, near the tip electrode. The pyroelectric material may also extend through the insulative sheath into the interior of the lead body.

Figure 4A:
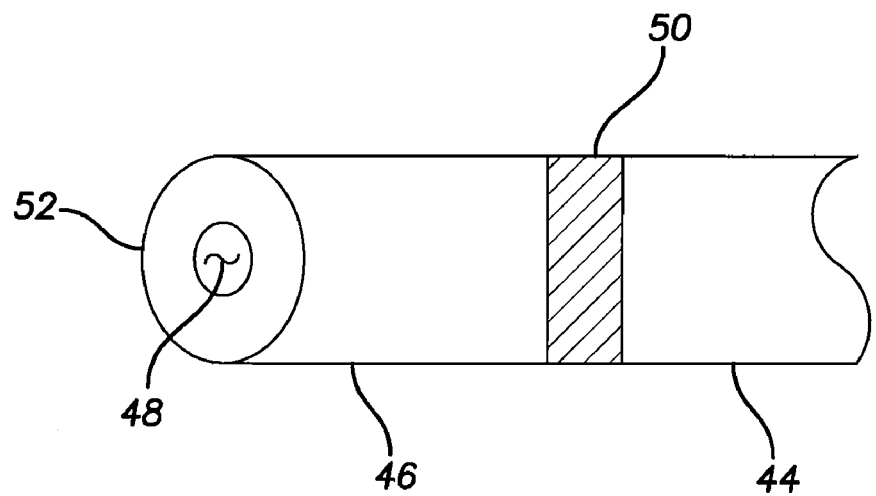
FIG. 4A is a simplified, perspective view of another illustrative lead body containing a pyroelectric material.

FIG. 4A illustrates a pyroelectric material coupled to a bipolar lead at its distal end as a collar. Lead body 44 at its distal end 46 contains a tip electrode 48, ring electrode 50, and a pyroelectric material 52 attached to the edge of the distal end of the lead body 44.

Figure 4B:
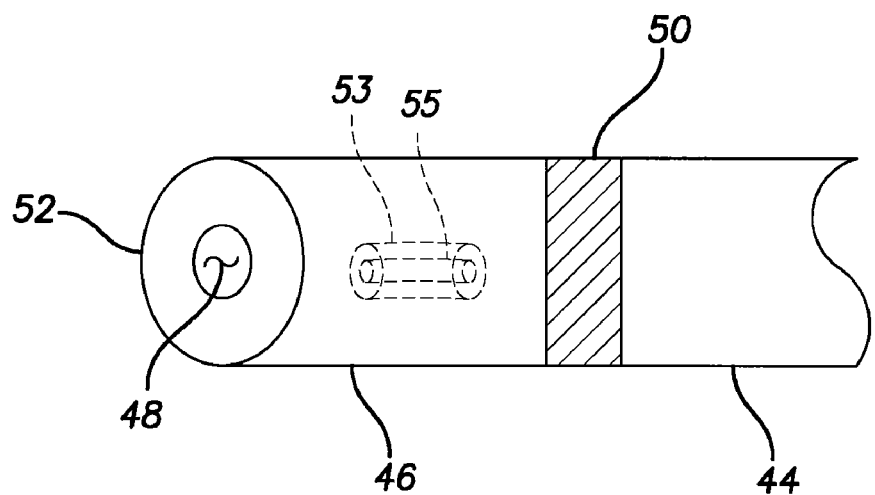
FIG. 4B is a simplified, perspective view of still another illustrative lead body containing a pyroelectric material.

In an alternative embodiment as illustrated in FIG. 4B, the pyroelectric material can be coupled to the distal end of the lead by its incorporation into the interior of the lead body behind the tip (distal) electrode, by using a pyroelectric material to form a plug 53. The plug 53 may encase a steroid 55, which elutes out when the lead is inserted into a patient, leaving behind the pyroelectric material which can absorb heat generated by radio frequency energy.

When the pyroelectric material absorbs heat generated by radio frequency energy, the resulting voltage generated by the pyroelectric material can be directed to an area that is less harmful to the patient. The redirection of the generated voltage can be accomplished in any suitable manner. For example, the voltage generated from the pyroelectric material may be led back to the pacing unit using an extra conductor coil or cable. The converted voltage signal can be interpreted using appropriate methods inside the pacing unit. Alternatively, the voltage generated from the pyroelectric material can be leaked as noise in the implantable cardiac device.

As alluded to above, the pyroelectric material can be applied to unipolar, bipolar leads, and multipolar leads; active fixation or passive fixation leads; and other types of medical electrical leads as are generally known in the art.

Example embodiments of the methods and components of leads containing a pyroelectric material, and devices containing such leads have been described herein. As noted elsewhere, these example embodiments have been described for illustrative purposes only, and are not limiting. Other embodiments are possible within the scope of the invention. Such embodiments will be apparent to persons skilled in the relevant art(s) based on the teachings contained herein.

Thus, the breadth and scope of the present invention should not be limited by any of the above-described exemplary embodiments, but should be defined only in accordance with the following claims and their equivalents.

What is claimed is:

1. A medical electrical lead capable of dissipating heat generated from radio frequency (RF) energy, comprising:
  a lead body having a proximal end and a distal end;
  an electrical conductor extending from the proximal end to the distal end of the lead body;
  an electrical connector coupled to the conductor at the proximal end of the lead body;

an electrode coupled to the conductor at the distal end of the lead body; and a biocompatible pyroelectric material directly contacting the electrode to absorb heat generated at the electrode by RF energy;

wherein the biocompatible pyroelectric material absorbs heat by converting the heat into an electrical charge.

2. The lead of claim 1, wherein the pyroelectric material comprises a polymeric material.

3. The lead of claim 1, wherein the biocompatible pyroelectric material comprises polyvinylidene fluoride (PVDF).

4. The lead of claim 3, wherein the pyroelectric material comprises at least one of a film, a mesh, a disk, a collar, a plug, or a combination thereof.

5. The lead of claim 4, wherein the pyroelectric material comprises a plug and the plug encases a steroid material.

6. The lead of claim 1, further comprising a second electrical conductor and a second electrode, the second conductor coupled to the electrical connector and extending to and coupled to the second electrode near the distal end of the lead body proximate of the first electrode.

7. The lead of claim 6, wherein the pyroelectric material comprises a polymeric material.

8. The lead of claim 7, wherein the polymeric material comprises PVDF.

9. The lead of claim 8, wherein the pyroelectric material is coupled to the lead between the first and second electrodes.

10. The lead of claim 9, wherein the pyroelectric material comprises at least one of a film, a mesh, a disk, a collar, a plug, or a combination thereof.

11. A method of making a medical electrical lead capable of dissipating heat generated from radio frequency (RF) energy comprising:

providing a medical electrical lead having a proximal end and a distal end and comprising an electrical conductor, an electrical connector coupled to the conductor at the proximal end of the lead, and an electrode coupled to the conductor at the distal end of the lead; and applying a biocompatible pyroelectric material directly to the electrode to dissipate heat generated at the electrode when subjected to RF energy.

12. The method of claim 11, whereby the pyroelectric material dissipates heat by absorbing and converting the heat to voltage.

13. The method of claim 11, comprising applying a pyroelectric polymer to the electrode near the distal end.

14. The method of claim 13, comprising applying a pyroelectric polymer comprising PVDF to the electrode near the distal end.

15. The method of claim 14, comprising forming a film, mesh, disk, collar, plug, or a combination thereof of the pyroelectric polymer.

16. The method of claim 15, comprising forming a plug of the pyroelectric polymer and encasing a steroid within the plug.

17. The method of claim 11, further comprising providing a second electrical conductor and a second electrode, the second conductor coupled to the electrical connector and extending to and coupled to the second electrode near the distal end of the lead proximate of the first electrode.

18. The method of claim 17, comprising applying a pyroelectric polymer to the lead near the distal end.

19. The method of claim 18, comprising applying a pyroelectric polymer comprising PVDF to the lead near the distal end.

20. The method of claim 19, comprising forming a film, mesh, disk, collar, plug, or a combination thereof of the pyroelectric polymer between the first and second electrodes.

21. The method of claim 20, comprising forming a plug of the pyroelectric polymer and encasing a steroid within the plug.

* * * * *